United States Patent [19]
Bertelli

[11] 4,183,954
[45] Jan. 15, 1980

[54] BENZOIC ACID DERIVATIVES AND THERAPEUTIC COMPOSITION CONTAINING THE SAME

[75] Inventor: Aldo Bertelli, Milan, Italy
[73] Assignee: Seuref A.G., Vaduz, Liechtenstein
[21] Appl. No.: 895,852
[22] Filed: Apr. 12, 1978
[30] Foreign Application Priority Data
Apr. 27, 1977 [FR] France .................. 77 12788
[51] Int. Cl.$^2$ ............... A61K 31/195; C07C 101/42; C07C 101/60
[52] U.S. Cl. ....................... 424/319; 424/316; 562/433; 562/442; 562/451; 562/452; 562/455
[58] Field of Search ............... 424/316, 319; 562/433, 562/451, 452, 455, 442

[56] References Cited
U.S. PATENT DOCUMENTS

| | | | |
|---|---|---|---|
| 3,364,249 | 1/1968 | Bolhofer | 562/455 X |
| 3,892,801 | 7/1975 | Kazan | 562/450 |
| 4,070,484 | 1/1978 | Harita et al. | 424/319 |

*Primary Examiner*—James O. Thomas, Jr.
*Assistant Examiner*—Vera C. Clarke
*Attorney, Agent, or Firm*—Young & Thompson

[57] ABSTRACT

This invention relates to compounds having the general formula:

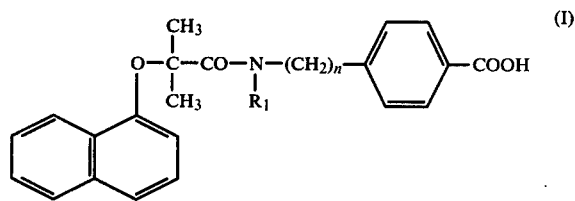

in which $R_1$ is a hydrogen atom or a lower alkyl radical and n is zero or an integer from 1 to 4, and their salts with therapeutically acceptable organic or inorganic bases.

Said compounds possess, in particular, choleretic, antiatherosclerotic, hypocholesterolemic and antiphlogistic activities.

6 Claims, No Drawings

BENZOIC ACID DERIVATIVES AND THERAPEUTIC COMPOSITION CONTAINING THE SAME

This invention relates to derivatives having the following general formula:

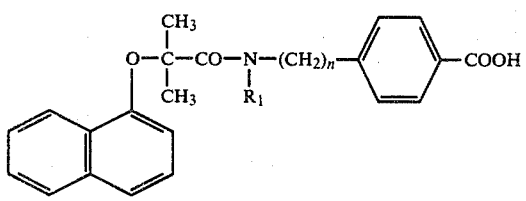

in which $R_1$ is a hydrogen atom or a lower alkyl radical and n is zero or an integer from 1 to 4.

A process for the preparation of compounds of formula (I), comprises condensing a compound having the formula:

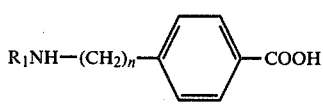

in which $R_1$ is a hydrogen atom or a lower alkyl radical and n is zero or an integer from 1 to 4, with α-naphthoxy-isobutyric acid chloride having the formula:

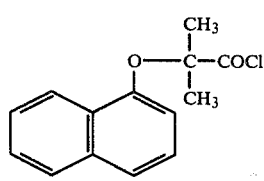

in the presence of an inert solvent, at the reflux temperature.

The condensation reaction is preferably effected while protecting the acid function of the compound of the formula (II), such as by prior addition of an organic base such as triethylamine, before reaction with α-naphthoxy-isobutyric acid chloride.

The solvent used is, for example, a halogenated hydrocarbon such as chloroform.

The following non-limiting Examples are given to illustrate the process for the preparation of compounds of this invention.

EXAMPLE 1

Preparation of p-[α-(α-naphthoxy)isobutyramido-]benzoic acid (a) Preparation of α-naphthoxy-isobutyric acid To prepare α-naphthoxy-isobutyric acid, α-naphthol (20 g), acetone (200 g), chloroform (19.5 g) and NaOH pellets (40 g) are reacted in a flask. The mixture is refluxed for about 4 hours. After cooling, an equal volume of water is added. To remove the unreacted acetone, the material is evaporated in vacuo and made acidic with dilute sulfuric acid. The resulting precipitate is filtered off and is then dissolved in a 5% bicarbonate solution. The resulting mixture is then heated and filtered through animal charcoal. The material is again made acidic and filtered, after which the product thus obtained is dried.

The resulting acid is recrystallized from ligroin until a white crystalline material having a melting point of 127°–130° C. is obtained.

(b) Preparation of α-naphthoxy-isobutyric acid chloride 2.3 g of the above acid are dissolved in 50 ml anhydrous benzene and thionyl chloride (2 g) is then added thereto. The reaction mixture is then refluxed for 2 hours, after which the solvent is evaporated off, the material is taken up into benzene and is again evaporated. The resulting product has an oily consistency.

(c) Condensation reaction with para-aminobenzoic acid

Triethylamine (3 moles) is added to a solution of para-aminobenzoic acid (slight excess) in chloroform; the mixture is heated to the reflux temperature and the above-prepared acid chloride dissolved in chloroform is added thereto. The reaction mixture is maintained for 2 hours at the boiling temperature, after which it is cooled and left aside for 10 hours. The solvent is evaporated off, the residue is made acidic with a 10% HCl solution, and the material is then extracted with ethyl acetate. The extract is dried over $Na_2SO_4$ and the ethyl acetate is evaporated off. The residue is recrystallized from benzene-ligroin 50:50, to give p-[α-(α-naphthoxy)-isobutyramido]benzoic acid, which is a white crystalline material soluble in bicarbonate and which has a melting point of 155° C.

EXAMPLES 2 AND 3

Using a procedure similar to that of Example 1, p-(α[α-(α-naphthoxy)isobutyryl]-α-methylamino)benzoic acid (compound 2) and p-[α-(α-naphthoxy)isobutyramidomethyl]benzoic acid (compound 3) are prepared, respectively.

The results of toxicological and pharmacological tests reported below demonstrate the properties of the compounds of the general formula (I), in particular a low toxicity together with choleretic, antiatherosclerotic, hypocholesterolemic and antiphlogistic activities.

Thus, the invention includes also within its scope a therapeutic composition having, in particular, choleretic, antiatherosclerotic, hypocholesterolemic and antiphlogistic activities, comprising as active ingredient an efficient amount of a compound of the formula (I) or its salts with pharmaceutically acceptable inorganic or organic bases, optionally together with suitable pharmaceutic carriers or diluents.

I—TOXICOLOGICAL TESTS

The determinations of the toxicity of p-[α-(α-naphthoxy)isobutyramido]benzoic acid effected according to the method of Lichtfield and Wilcoxon show that, on intraperitoneal administration, the $LD_{50}$ is 425 mg/kg in rats and 395 mg/kg in mice. On oral administration, the $LD_{50}$ obtained is 2.2 g in rats and 2.5 g in mice.

The chronic toxicity tests confirmed the low toxicity of the product. The administration of 50 mg/kg of the compound, for a period of time of 3 months, did not induce any intolerance and any toxicity. The determinations regularly effected with respect to blood, glycemia, transaminases, urinary excretion and azotemia in the treated rats failed to disclose any significant change or pathological modification, both at the beginning and at the end of the treatment.

II—PHARMACOLOGICAL TESTS

(1) Choleretic activity

Oral administration of the test compound at a dosage of 100 mg/kg, and intraperitoneal administration of the test compound at a dosage of 20 mg/kg induce a significant increase of choleresis in rats. The increase of the choleresis is more substantial and more extended than that induced by dehydrocholic acid. The increase concerns the elimination of either the biliary pigments or cholesterol.

(2) Anti-steatotic activity

Administration of the test material to rats at a daily dosage of 50 mg/kg inhibits the hepatic steatosis and the hypercholesterolemia induced by Handler's steatogenic diet.

(3) Hypocholesterolemic activity

Administration of 100 mg/kg by the intraperitoneal route, or of 300 mg/kg by the oral route of the test compound inhibits the hypercholesterolemia induced in rats by the intraperitoneal injection of 200 mg/kg Twin-Triton.

(4) Antiphlogistic activity

Intraperitoneal or oral administration of the test material at dosages within the range of from 50 mg/kg to 300 mg/kg inhibits the experimental phlogistic reaction induced in rats.

Administration of the test compound inhibits, in particular, the oedema of the rat's paw induced by dextran and carageenin and also the granulomatous reaction induced by the sub-cutaneous penetration of foreign bodies (Experimental granuloma test).

(5) Antianaphylactic activity

Administration to rats of the test compound at a dosage of 60 mg/kg by the oral route or of 50 mg/kg by the intraperitoneal route inhibits the anaphylactic reaction and the death induced in guinea-pigs sensitized with horse serum.

The results of the above-reported tests demonstrate the low toxicity and the valuable choleretic, antiatherosclerotic, hypocholesterolemic and antiphlogistic properties of the derivatives of this invention which make them therapeutically useful in human medicine.

For oral administration, the therapeutic composition of this invention may be formulated as tablets, capsules, powders, granules, drops or syrups. It may also be formulated, for parenteral administration, as injectable solutions and, for rectal administration, as suppositories, in unit dosage form. Each unit dose contains advantageously 0.020–0.500 g active ingredient. The daily dosage regimen may vary within the range of from 0.02 to 1.00 g active ingredient, according to the age of the patient and the condition to be treated.

Non-limiting Examples of pharmaceutic formulations including the compounds of this invention are given below.

| Tablets | |
|---|---|
| Compound 1 | 0.025 to 0.05 g |
| Conventional excipients | |
| Capsules | |
| Compound 2 | 0.025 to 0.05 g |
| Conventional excipients | |
| Injectable ampoules | |
| Compound 1 | 0.02 to 0.05 g |
| Excipient: isotonic solvent, sufficient to make | 3 ml |
| Syrup | |
| Compound 3 | 0.1 to 0.25 g |
| Excipient: aqueous alcoholic solution, sufficient to make | 100 ml |
| Suppositories | |
| Compound 1 | 0.2 to 0.5 g |
| Conventional excipients | |

The therapeutic composition of this invention may be profitably administered to human patients in the treatment of hepatobiliary conditions, of choleresis and of atherosclerotic and cholesterolemic conditions.

Having now described my invention what I claim as new and desire to secure by Letters Patents is:

1. Compounds having the general formula:

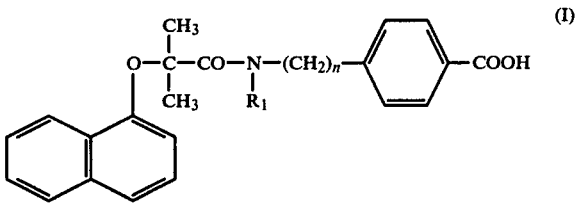

in which $R_1$ is a hydrogen atom or a lower alkyl radical and n is zero or an integer from 1 to 4, and their salts with therapeutically administrable inorganic or organic bases.

2. p-[α-(α-Naphthoxy)isobutyramido]benzoic acid and its addition salts with therapeutically administrable inorganic or organic bases.

3. p-(α-[α-(α-Naphthoxy)isobutyryl]-α-methylamino)benzoic acid and its addition salts with therapeutically administrable inorganic or organic bases.

4. p-[α-(α-Naphthoxy)isobutyramidomethyl]benzoic acid and its addition salts with therapeutically administrable inorganic or organic bases.

5. A therapeutic composition having, in particular, choleretic, antiatherosclerotic, hypocholesterolemic and antiphlogistic activities comprising, as active ingredient, an effective amount of a compound having the general formula:

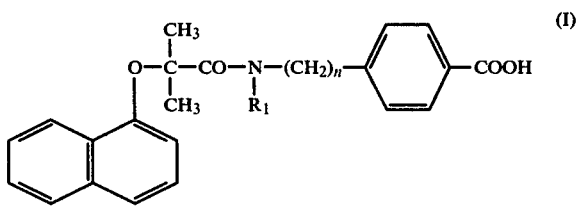

in which $R_1$ is a hyrogen atom or a lower alkyl radical and n is zero or an integer from 1 to 4, and their salts with therapeutically administrable inorganic or organic bases, and a therapeutically acceptable carrier.

6. A therapeutic composition as claimed in claim 5, in unit dosage form, each unit dose containing 0.020–0.500 g of active ingredient.

* * * *